United States Patent [19]

Lester et al.

[11] Patent Number: 4,526,573
[45] Date of Patent: Jul. 2, 1985

[54] SUCTION-IRRIGATION EQUIPMENT WITH CONTROL VALVE

[75] Inventors: Graham G. Lester, Folkestone; Peter J. Brand, Hythe; Graham Deane, Ascot, all of England

[73] Assignee: Smiths Industries Public Limited Company, London, England

[21] Appl. No.: 477,550

[22] Filed: Mar. 21, 1983

[30] Foreign Application Priority Data

Mar. 29, 1982 [GB] United Kingdom ............ 8209131

[51] Int. Cl.³ .............................................. A61M 1/00
[52] U.S. Cl. ...................................... 604/33; 433/95; 604/119; 604/902
[58] Field of Search ........................ 604/30, 33, 35, 54, 604/73, 118, 119, 902, 249, 27; 137/625.69; 433/91, 92, 95, 100; 156/73.1, 245, 293; 264/248, 250

[56] References Cited

U.S. PATENT DOCUMENTS

| 1,843,169 | 2/1932 | McKesson | 604/30 |
| 2,812,765 | 11/1957 | Tofflemire | 604/35 |
| 3,279,748 | 10/1966 | Coulter | 137/625.69 |
| 3,944,261 | 3/1976 | Reed et al. | 156/73.1 |
| 4,193,406 | 3/1980 | Jinotti | 604/33 |
| 4,211,588 | 7/1980 | Raines | 156/73.1 |
| 4,451,257 | 5/1984 | Atchley | 604/33 |

Primary Examiner—C. Fred Rosenbaum
Assistant Examiner—J. L. Kruter
Attorney, Agent, or Firm—Pollock, VandeSande and Priddy

[57] ABSTRACT

A suction irrigator, particularly for surgical use, is made as two units of plastics material. One unit is formed by a handle having first and second parallel bores which are coupled respectively to a suction source and a source of irrigating fluid. The other unit comprises a valve assembly the housing of which is formed by injection moulding. The valve assembly has two inlet conduits which are inserted within respective bores in the handle, and an outlet conduit which can be connected to one or the other of the inlet conduits by displacing a valve member. The bores extend along tubular formations in the handle which are linked along most of their length by a land but which are separated by a slit close to the valve. On the handle there is a lip positioned to engage a resilient catch on the valve member and thereby limit its displacement.

9 Claims, 7 Drawing Figures

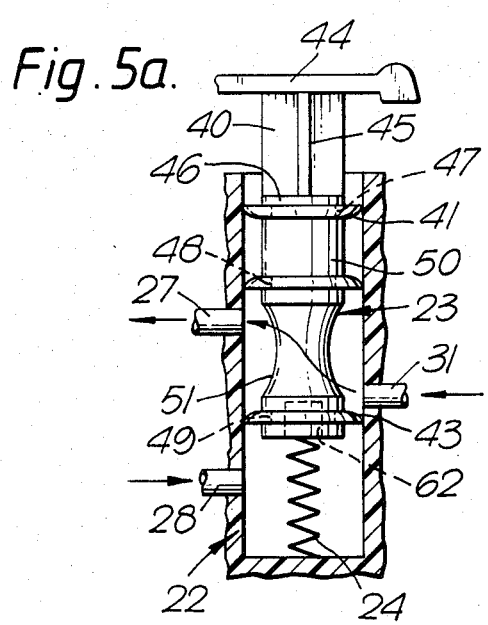
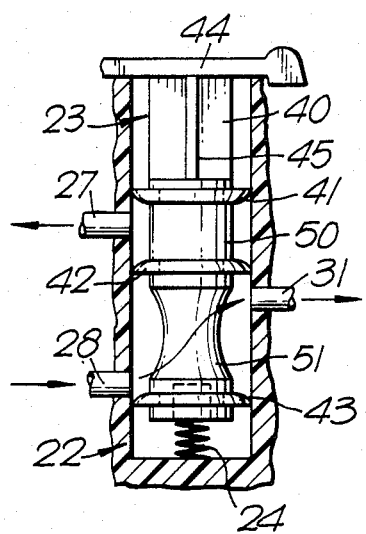
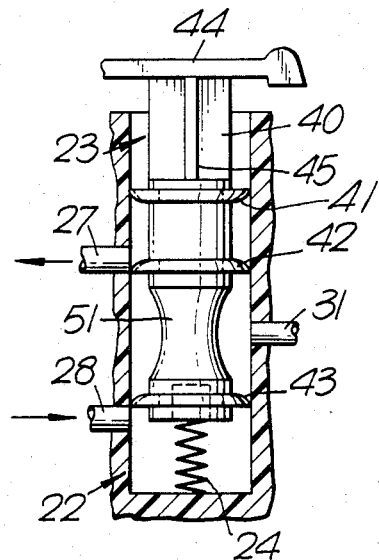

SUCTION-IRRIGATION EQUIPMENT WITH CONTROL VALVE

BACKGROUND OF THE INVENTION

This invention relates to suction-irrigation equipment.

The invention is more particularly concerned with suction-irrigation equipment for hand-held medical use, such as, of the kind used for cleaning wounds during surgery.

One form of suction irrigator has a handle provided with two conduits connected respectively to a source of irrigating fluid and a suction source. The suction irrigator has a valve assembly connected to the conduits, and a single outlet that can be connected to one or the other of the conduits by operation of the valve assembly so that the outlet can be used to supply irrigating fluid or to apply suction. Preferably, the equipment is made at low cost of a plastics material so that it can be discarded after a single use.

In order to ensure reliable, leak-proof operation, the valve assembly must be made accurately to small tolerances; if of plastics material it can be made by injection moulding. The disadvantage of this, however, is that this is a relatively costly process especially for large mouldings. Since the handle of the suction irrigator must be sufficiently long to fit comfortably and securely in the hand of the user, this makes the entire equipment fairly large, and consequently expensive to make by accurate moulding techniques, such as, injection moulding.

BRIEF SUMMARY OF THE INVENTION

It is an object of the present invention to provide suction-irrigation equipment, and a method of manufacture of such equipment that may be used to alleviate the abovementioned difficulties.

According to one aspect of the present invention there is provided suction-irrigation equipment of the kind including: a handle having a first bore adapted for connection to a suction source, and a second bore adapted for connection to a source of irrigating fluid; valve means connected with said first and second bores; and a single outlet port connected with said valve means, said valve means being operable to connect said first or second bores to said outlet port, wherein said handle is formed as a first unit, and said valve means and outlet port are formed as a second unit separate from said first unit, said first and second units being subsequently joined together.

In this way, the valve means may be made by an accurate moulding technique whereas the handle can be made cheaply by a less-accurate technique.

The first unit may be substantially of plastics material, and said valve means may include a housing substantially of plastics material which may be an injection moulding. The valve means may be connected with the handle by means of first and second conduits on said valve means which are received within respective first and second bores. The first and second bores may extend substantially parallel to one another and may be provided in tubular formations, said tubular formations being linked together along their length except in a region close to said valve means, such that the ends of said tubular formations close to said valve means can be flexed towards or away from one another to facilitate connection with said valve means. The valve means may include a valve member that is displaceable transversely of said first and second bores, the valve member being provided with an engagement member that is arranged to engage a projecting lip on said handle so as to limit transverse displacement of said valve member in one direction. The engagement member may be urged resiliently against the lip. The equipment may include a length of flexible tubing having first and second parallel bores extending along its length, one end of said tubing being coupled with said handle, the bores of said tubing making connection with respective bores of said handle.

According to another aspect of the present invention there is provided a method of manufacture of suction irrigation equipment comprising the steps of: making a handle having first and second bores extending therethrough; making valve means having a housing which includes first and second inlet ports that are arranged to align with said first and second bores, and an outlet port that is arranged for interconnection with one or the other of said first and second inlet ports; and joining said valve means with said handle such that said first and second inlet ports connect with said first and second bores.

The valve means may include a valve member that is inserted in said valve housing after joining said valve means with said handle.

A medical suction irrigator and its method of manufacture, in accordance with the present invention, will now be described, by way of example, with reference to the accompanying drawings.

BRIEF DESCRIPTION OF THE DRAWINGS

FIGS. 5a, 5b and 5c show the valve of the suction irrigator in greater detail, in three different positions.

DETAILED DESCRIPTION

Figure 1:
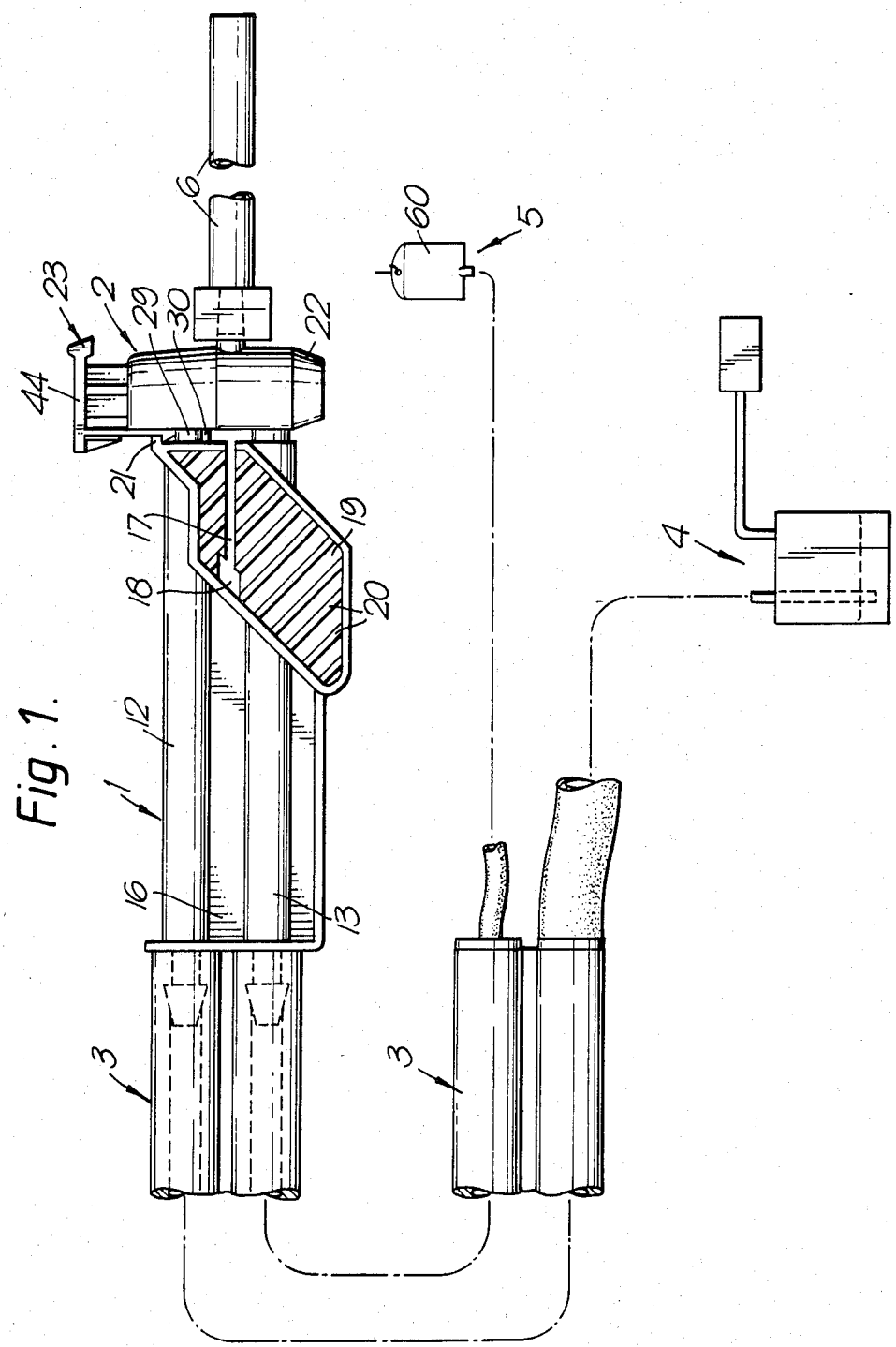
FIG. 1 is a side elevation view of the suction irrigator.
Figure 2:
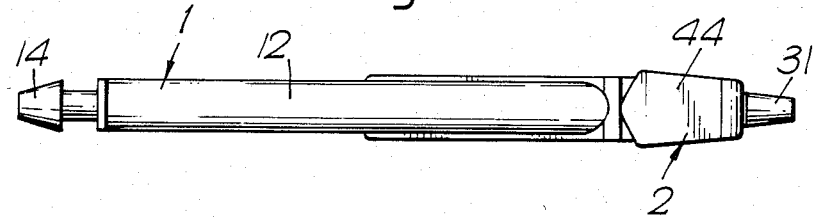
FIG. 2 is a plan view of the suction irrigator of FIG. 1.
Figure 3:
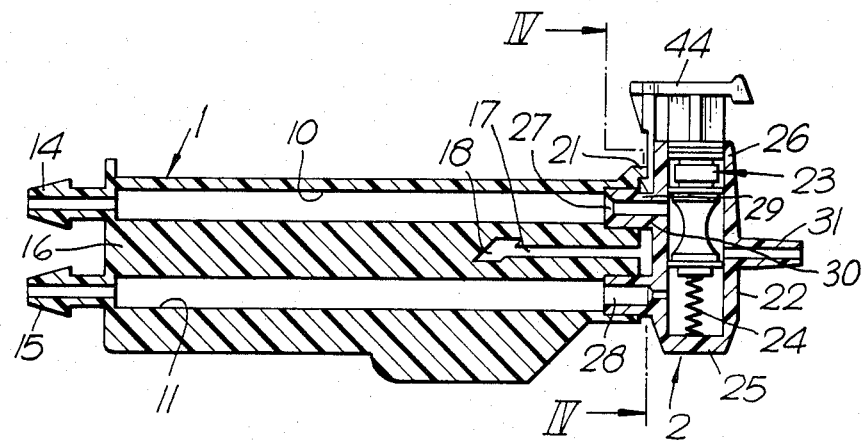
FIG. 3 shows the suction irrigator in section.

With reference to FIGS. 1 to 3, the suction irrigator is in two parts, namely, a handle 1 and a valve assembly 2. The suction-irrigation system comprises double tubing 3 which connects the suction irrigator with a suction source 4 and a source of irrigation fluid 5. A probe 6 is fitted to the valve assembly 2 which is operable to connect the probe to the suction source 4 or the source of irrigation fluid 5.

With reference now especially to FIG. 3, the handle 1 is a unitary assembly of a rigid plastics material and may be made as a two-part moulding. The handle 1 is of generally rectangular shape and has two cylindrical bores 10 and 11 which run along the handle from its rear end to its forward end through tubular formations 12 and 13. At their rear ends the bores 10 and 11 are terminated with tapered spigots 14 and 15 which are received within respective bores at the forward end of the double tubing 3. The tubular formations 12 and 13 are linked by a central flat land 16 that extends along the length of the handle 1. At its forward end, the land 16 is formed with a slit 17 that extends parallel to the tubular formations 12 and 13 and that is slightly enlarged at its rear end 18. A lozenge-shape grip portion 19 (FIG. 1) is formed at the forward end of the handle 1 by raised ribs 20 extending across the tubular formations 12 and 13 and the land 16. Above the forward end of the upper tubular formation 12 the handle is formed with a small lip 21, the purpose of which will become apparent later.

The valve assembly 2 is shown most clearly in FIGS. 3 and 5a to 5c. The assembly comprises three parts: an outer housing 22, a valve member 23, and a spring 24. The housing 22 is a precision plastics injection moulding of generally cylindrical shape, having a closed lower end 25 and an open upper end 26. On one side of the housing 22 are provided two inlet ports 27 and 28 spaced apart along the housing, the lower port 28 being arranged to fit within the forward end of the irrigation fluid bore 11 while the upper port 27 is similarly received within the end of the suction bore 10. Both ports 27 and 28 are provided by short parallel conduits projecting from the housing 22, the upper conduit being waisted close to the body of the housing to form a portion 29 of reduced external diameter that is reinforced by a web 30 extending along its lower edge. From the other side of the housing 22 there extends an outlet conduit or port 31 which is positioned between the two inlet ports and parallel with them. The outer surface of the outlet conduit is formed with a luer-taper for receiving the probe 6.

The three ports 27,28 and 31 communicate with the interior of the body of the housing 22 which is accurately dimensioned and of cylindrical shape. The interior of the housing 22 contains the valve member 23 and the spring 24, the spring bearing on the lower end 25 of the housing and acting to urge the valve member 23 upwardly, transversely of the ports 27,28 and 31.

The valve member 23 has a rigid plastics body or stem 40 on which are mounted three resilient, elastomeric sealing flanges 41,42 and 43 that contact the internal surface of the housing 22. At its upper end, the stem 40 has a flat horizontal plate 44 on which the user places his finger or thumb to displace the valve member against the action of the spring 24. Beneath the plate 44 the stem has a short portion 45 of cruciform shape that terminates in a flat circular plate 46. Below the plate 46 the valve stem is of circular cross-section and is provided with three annular grooves 47,48 and 49 in which the sealing flanges 41 to 43 respectively are mounted. The flanges 41 to 43 are each dished such that the outer edges of the middle and lower flanges 42 and 43 are normally below their inner edges, that is, are convex when viewed from above; the upper flange 41 is mounted the other way up so that its outer edge is above its innner edge, thereby being concave when viewed from above. The upper flange 41 and the middle flange 42 are separated by a short cylindrical section 50 of the valve stem 40. The middle flange 42 and the lower flange 43 are separated by a waisted section 51 of concave profile. At its lower end the stem 40 has a central recess 62 in which the upper end of the steel spring 24 is received.

Figure 4:
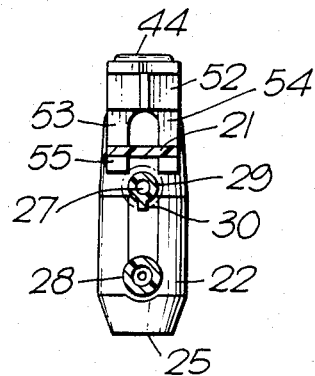
FIG. 4 is a sectional view along the line IV—IV of FIG. 3.

At the other end of the valve stem 40, the top plate 44 is provided with a downwardly-extending catch member 52 of generally inverted 'U'-shape (FIG. 4). When the stem 40 is located in the housing 22, the catch member 52 extends between the outside of the housing and the forward end of the handle 1. The catch member 52 has two arms 53 and 54 which extend down opposite sides of the port 27 astride its portion 29 of reduced diameter. On their rear surfaces the arms 53 and 54 are both provided with a raised tooth 55 that is arranged to engage the lower edge of the lip 21 so as thereby to limit upward travel of the valve member 23.

The suction irrigator is readily assembled by joining the valve housing 22 with the handle 1. In this respect, an adhesive or solvent may be applied to the outer surface of the ports 27 and 28, or to the forward end of the bores 10 and 11 so that the tow parts are securely joined. The valve member 23 and spring 24 may be assembled before or after the housing 22 has been joined to the handle 1 since the resilience of the catch member 52 enables it to be pushed downwardly over the lip 21 to snap into position.

The suction irrigator would normally be used with the removable probe 6. The probe 6 is a single-bore tube that is formed at its rear end with a Luer-tapered connector that can be push fitted over the outlet port 31. The probe 6 may be different shapes and sizes according to the use to which it is to be put. Preferably, the internal diameter of the probe is less than that of the port 31 so that any blockage that might occur takes place within the probe. In this way, the probe can be readily replaced if the blockage cannot be removed.

In its natural position, the valve stem 40 is urged to its upper limit of its travel by the spring 24 until the catch member 52 engages the lip 21. This position is shown in FIG. 5a and it can be seen that the lower flange 43 on the valve stem is situated intermediate the outlet port 31 and the irrigation port 28 thereby effectively sealing the irrigation port from the outlet port. The middle flange 42 is situated just above the suction port 27 so that fluid is enabled to flow between the outlet port 31 and the suction port around the waisted section 51 of the valve stem. In this position therefore suction is applied to the outlet port 31 and the probe 6.

When the valve member 23 is depressed fully by pushing on the plate 44, as shown in FIG. 5b, the middle flange 42 moves to a position intermediate the outlet port 31 and the suction port 27 whereas the lower flange 43 lies just below the irrigation port 28. In this position therefore the irrigating fluid is free to flow from the port 28 to the outlet port 31, and from there to the probe 6.

It is also possible to position the valve member 23 so that the outlet port 31 is sealed from both the irrigation and suction sources. This position is shown in FIG. 5c and relies on positioning the middle flange 42 just below the suction port 27, and the lower flange just above the irrigation port 28.

The sealing flanges 41 to 43 are oriented so as to improve the seal with the wall of the housing 22; more particularly, they are arranged so that the pressure exerted on either side of each flange operates to urge them into closer contact with the wall of the housing. In the suction position, shown in FIG. 5a, the pressure of irrigating fluid supplied to the lowest port 28 will force the outer edge of the lower flange 43 upwards into a more flat shape. Flattening the flange 43 will tend to give it a greater external diameter thereby bringing its outer edge into closer contact with the wall of the housing 22. The suction applied to the upper port 27 will also tend to flatten the lower flange 43 but because the suction port 27 is open to atmosphere via the outlet port 31, the pressure above the lower flange 43 will be substantially the same as atmospheric pressure. The suction will tend to make the seal provided by the middle flange 42 less effective but any leakage past this flange will be stopped by the upper flange 41 which is oriented such as to give an improved seal when suction is applied beneath it.

In the irrigation position, shown in FIG. 5b, the lower flange 43 moves below the irrigation port 28 and trapped fluid beneath the flange, in the lower part of the housing 22 will tend to force the flange into closer contact with the housing. The effectiveness of the seal provided by the lower flange 43 is, however, not so important in the irrigation mode since any leakage past the flange will be contained within the housing. In this position, the suction port 27 is sealed off below by the middle flange 42 and above by the upper flange 41. These flanges 41 and 42 both present convex surfaces to the port 27 so that the reduced pressure in the chamber defined between the two flanges tends to deform them into closer contact with the housing 22.

In the neutral position shown in FIG. 5c, the suction conduit 27 is also sealed between the upper and middle flanges 41 and 42, while the lower flange is situated just above the irrigation conduit 28 so that it seals the irrigation conduit in the same manner as in the suction mode.

In the suction mode, the user simply places the tip of the probe 6 close to the material to be removed and this is drawn through the probe and the suction bore 10 into the appropriate bore of the double tubing 3. To irrigate, the user depresses the valve member 23 to its fullest extent and the irrigation fluid—which may be supplied from a suspended bag 60 of saline solution—passes out of the tip of the probe. Placement of the probe tip can, in some circumstances, be made easier by partially depressing the valve member to the neutral position shown in FIG. 5c so that the outlet port 31 is sealed off.

The suction irrigator can be used for picking up and placing material such as tissue. To do this, the equipment is placed in the suction mode and the tip of the probe 6 is placed in contact with the material to be transferred, thereby causing it to be attracted to the probe. The material can then be lifted to a new location. When the material is correctly located, the valve member 23 is depressed so that the equipment is switched to the irrigating mode thereby causing the material to be forced off the end of the probe 6 by the pressure of fluid within it. Minor blockages that might occur in the suction mode can be cleared by changing to the irrigation mode so that the obstruction is forced out of the probe 6.

Because only a single bore outlet conduit and probe are used, this can be narrower than previous double conduit arrangements thereby making the equipment easier to use in restricted places.

The suction-irrigation equipment, in use, is connected to a standard suction source and irrigation source. The means by which these connections are made will generally be different and require special adaptors. By using a length of double or Siamese tubing the adaptors may be located remote from the suction-irrigation equipment so that it is not made unduly bulky or heavy.

Since the valve assembly 2 is made separate from the handle 1 it can be manufactured to high accuracy whereas the handle can be made more cheaply by less accurate moulding techniques. Because the valve assembly 2 is relatively small this simplifies the moulding process and keeps costs to a minimum. Dimensional tolerances for the handle 1 can be relatively large since the slit 17 enables the forward ends of the bores 10 and 11 to be flexed towards or away from each other slightly, so that they can be fitted over the ports 27 and 28 of the valve assembly 2.

It will be appreciated that various alternative valves could be used and that the equipment is not confined to medical use.

What we claim is:

1. Suction-irrigation equipment comprising a substantially rigid handle formed as a first unit, said first unit being an integral one-piece plastics molding, said molding having first and second tubular formations extending along the handle that are linked along their length by an integral land between said tubular formations, said tubular formations defining respective first and second bores extending therethrough, said unit having first and second projections at one end in communication respectively with said first and second bores, said projections being adapted for insertion within respective bores of flexible tubing connected to a suction source and a source of irrigating fluid, valve means formed as a second unit, said valve means having a valve housing and a valve member, said housing having an outlet port and first and second inlet ports, said valve member being displaceable within said housing to connect said first or second inlet ports to said outlet port, means connecting the other end of said first unit with said valve housing so that said first and second inlet ports communicate with said first and second bores respectively, and the said other end of said first unit having a gap in the said land to enable the ends of said tubular formations adjacent said other end of said first unit to be flexed towards or away from one another to facilitate connection of said first unit with said valve housing.

2. Suction-irrigation equipment according to claim 1, wherein the housing of said valve means is of injection moulded plastics material.

3. Suction-irrigation equipment according to claim 1, wherein said valve housing includes a first and second conduit within which said first and second inlet ports respectively are formed, said first and second conduits being received within respective first and second bores in said handle.

4. Suction-irrigation equipment according to claim 1, wherein said first and second bores extend substantially parallel to one another.

5. Suction-irrigation equipment according to claim 4, wherein said valve means is displaceable along said housing transversely of said first and second bores.

6. Suction-irrigation equipment according to claim 5, wherein said handle has a projecting lip, said valve member including an engagment member that is located to engage said lip so as thereby to limit transverse displacement of said valve member in one direction.

7. Suction-irrigation equipment according to claim 6, wherein said engagement member is urged resiliently against said lip.

8. Suction-irrigation equipment according to claim 1, including a probe member and means removably coupling said probe member with said outlet port.

9. A suction-irrigation system comprising a suction source, a source of irrigating fluid, flexible tubing having bores therein connected at one end respectively with said suction source and said source of irrigating fluid, a substantially rigid handle formed as a first unit, said first unit being an integral one-piece plastics molding, said molding having first and second tubular formations extending along the handle that are linked along their length by an integral land between said tubular formations, said tubular formations defining respective first and second bores extending therethrough, said unit having first and second projections at one end through which said first and second bores extend, said projections being inserted in respective bores in the other end of said flexible tubing, valve means formed as a second unit separate from said first unit, said valve means having a valve housing and a valve member, said housing having an outlet port and first and second inlet ports, said valve member being displaceable along said housing to connect said first or second inlet ports to said outlet port, means connecting the other end of said first unit with said valve housing so that said first and second inlet ports communicate with said first and second bores respectively, and the said other end of said first unit having a gap in the said land to enable the ends of the tubular formations adjacent said other end of said first unit to be flexed towards or away from one another to facilitate connection of said first unit with said second unit.

* * * * *